United States Patent
Jurna et al.

(10) Patent No.: US 11,324,948 B2
(45) Date of Patent: May 10, 2022

(54) DEVICE FOR RADIO-FREQUENCY SKIN TREATMENT

(71) Applicant: KONINKLIJKE PHILIPS N.V., Eindhoven (NL)

(72) Inventors: Martin Jurna, Eindhoven (NL); Marco Baragona, Eindhoven (NL); Margaret Ruth Horton, Eindhoven (NL); Jonathan Alambra Palero, Eindhoven (NL); Hendrik Halling Van Amerongen, Eindhoven (NL); Babu Varghese, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 561 days.

(21) Appl. No.: 15/746,023

(22) PCT Filed: Jul. 11, 2016

(86) PCT No.: PCT/EP2016/066377
§ 371 (c)(1),
(2) Date: Jan. 19, 2018

(87) PCT Pub. No.: WO2017/012895
PCT Pub. Date: Jan. 26, 2017

(65) Prior Publication Data
US 2018/0207421 A1    Jul. 26, 2018

(30) Foreign Application Priority Data
Jul. 21, 2015  (EP) ..................................... 15177699

(51) Int. Cl.
*A61N 1/32*    (2006.01)
*A61N 1/04*    (2006.01)
(Continued)

(52) U.S. Cl.
CPC .............. *A61N 1/328* (2013.01); *A61B 18/14* (2013.01); *A61N 1/0476* (2013.01);
(Continued)

(58) Field of Classification Search
CPC ...... A61N 1/328; A61N 1/0492; A61N 1/403; A61N 1/0476; A61N 1/00–445;
(Continued)

(56) References Cited

U.S. PATENT DOCUMENTS 4,304,235 A    12/1981  Kaufman
4,934,383 A *  6/1990  Glumac ............... A61N 1/0456
                                                       607/152
(Continued)

FOREIGN PATENT DOCUMENTS

WO          8100785 A1     3/1981
WO      WO-8100785 A1 *    3/1981  ............. H01B 1/122
(Continued)

*Primary Examiner* — Joseph A Stoklosa
*Assistant Examiner* — Adam J Avigan

(57) ABSTRACT

A device for (RF) skin treatment comprising an active electrode having a first skin contact surface for electrical contact with a skin of a user and during use A return electrode having a second skin contact surface for electrical contact with the skin of the user during use. An RF generator to supply an RF treatment voltage between the active electrode and the return electrode to heat the skin below the active electrode. A coupling member arranged on the first skin contact surface comprising an electrically conductive material to improve the electrical coupling of the active electrode to the skin surface. The coupling member comprising a first layer of a first electrically conductive material arranged on the first skin contact surface, and a second layer of a second electrically conductive material, arranged on a side of the first layer remote from the first skin contact surface.

19 Claims, 5 Drawing Sheets

(51) Int. Cl.
*A61B 18/14* (2006.01)
*A61B 18/00* (2006.01)
*A61N 1/40* (2006.01)

(52) U.S. Cl.
CPC .......... *A61N 1/0492* (2013.01); *A61N 1/403* (2013.01); *A61B 2018/0047* (2013.01); *A61B 2018/00071* (2013.01); *A61B 2018/00107* (2013.01); *A61B 2018/00136* (2013.01); *A61B 2018/00178* (2013.01); *A61B 2018/00202* (2013.01); *A61B 2018/00452* (2013.01)

(58) Field of Classification Search
CPC .......... A61B 18/14; A61B 2018/0047; A61B 2018/00107; A61B 2018/00136; A61B 2018/00071; A61B 2018/00178; A61B 2018/00202; A61B 2018/00452; A61B 18/00–28; A61B 2018/00005–266
See application file for complete search history.

(56) References Cited

U.S. PATENT DOCUMENTS

| | | | |
|---|---|---|---|
| 4,970,954 A * | 11/1990 | Weir | B41K 1/42 101/104 |
| 5,919,219 A | 7/1999 | Knowlton | |
| 2004/0162602 A1 | 8/2004 | Cohen | |
| 2004/0210214 A1 * | 10/2004 | Knowlton | A61N 7/00 606/41 |
| 2007/0032719 A1 * | 2/2007 | Menon | C09J 133/06 600/391 |
| 2010/0082079 A1 * | 4/2010 | Skahan | A61N 1/0456 607/46 |
| 2011/0245653 A1 | 10/2011 | Varahramyan | |
| 2012/0283725 A1 | 11/2012 | Knowlton | |
| 2013/0085551 A1 * | 4/2013 | Bachinski | A61N 1/36021 607/59 |
| 2013/0123587 A1 | 5/2013 | Sarrafzadeh | |
| 2013/0289679 A1 * | 10/2013 | Eckhouse | A61N 1/06 607/102 |
| 2014/0065664 A1 | 3/2014 | Aknine | |
| 2014/0207217 A1 * | 7/2014 | Lischinsky | A61B 18/1206 607/102 |

FOREIGN PATENT DOCUMENTS

| | | |
|---|---|---|
| WO | 2010093319 A1 | 8/2010 |
| WO | 2012023129 A1 | 2/2012 |
| WO | 2012073232 A1 | 6/2012 |
| WO | 2014160848 A1 | 10/2014 |
| WO | 2015185583 A1 | 12/2015 |

* cited by examiner

DEVICE FOR RADIO-FREQUENCY SKIN TREATMENT

This application is the U.S. National Phase application under 35 U.S.C. § 371 of International Application No. PCT/EP2016/066377, filed on Jul. 11, 2016, which claims the benefit of International Application No. 15177699.4 filed on Jul. 21, 2015. These applications are hereby incorporated by reference herein.

FIELD OF THE INVENTION

The invention relates to a device for radio-frequency (RF) treatment of human skin, wherein the device comprises a coupling member for electrically coupling one or more electrodes of the device to the skin. The invention also relates to a coupling arrangement comprising a coupling member for electrically coupling one or more electrodes of an RF skin treatment device to the skin. The device according to the invention is primarily suitable for fractional RF skin treatment, in particular for the formation of non-ablative lesions in the skin.

BACKGROUND OF THE INVENTION

Radio-frequency (RF) electrical energy is conventionally used in both the professional and the home-use aesthetics market for skin tightening. The ability of large-volume heating at dermal skin level has made the radio-frequency technology a standard for skin tightening and for treating skin laxity. Compared to laser-based skin treatment devices, RF skin treatment devices have a relatively low cost price and can provide treatment of relatively large volumes of skin and treatment of relatively deep target positions in the skin. Additionally, the dissipation of RF electrical energy by skin tissue does not rely on specific absorption properties of chromophores or skin tissues, so that the delivery of RF electrical energy to the skin tissue is not influenced by, for example, different tissue pigmentation levels.

The basic principle of RF electrical energy delivery to skin tissue is that an alternating RF electrical current is applied by electrodes in a closed circuit with the skin. The skin tissue impedance directly affects the extent of the heating. RF electrical current propagates more easily through tissues with a high electrical conductivity, i.e. with a low electrical resistance, while tissues with a high electrical resistance, i.e. with a high impedance and a low electrical conductivity, are poor conductors of RF electrical energy. The RF energy follows a path through the skin tissue having the least electrical resistance and is dissipated as thermal energy primarily due to molecular vibrations.

A growing application for RF skin treatment beyond skin tightening is skin rejuvenation, wherein fractional thermal lesions are simultaneously created in superficial layers of the skin, using one or more relatively small active electrodes. Recently, different professional devices have been launched on the aesthetics market addressing skin rejuvenation with a radio-frequency treatment device. Skin rejuvenation provides a combination of different consumer benefits, such as an even skin tone, a reduction of pigmentation spots, an improved radiance of the skin, and a reduction of fine lines and other skin texture. When applying RF electrical energy for the purpose of skin rejuvenation, the RF energy is primarily used to damage the stratum corneum and the epidermis, possibly including the dermal-epidermal junction and the top layer of the dermis. Traditional laser-based skin rejuvenation treatments are performed by means of ablative or non-ablative settings of laser light having a wavelength highly absorbed by water, whereby ablative treatments vaporize the skin tissue and create hollow pillars in the skin, and non-ablative treatments heat the skin to a temperature in a range of 65° C. to 100° C. to initiate cell necrosis, collagen denaturation, collagen contraction, and eventually collagen remodeling.

In co-pending patent application EP 14171193.7, filed by applicant, an RF skin treatment device having a centro-symmetric RF electrode configuration is described. The RF skin treatment device comprises a relatively small active center electrode having a diameter between 100 µm and 500 µm and a larger return electrode surrounding the active center electrode. The centro-symmetric RF electrode configuration concentrates heating of the skin to positions immediately below the small active electrode, which results in a localized damaged zone in superficial layers of the skin leading to skin rejuvenation. By applying a plurality of active electrodes surrounded by return electrodes, a fractional pattern of damaged zones is provided, wherein each damaged zone is surrounded by healthy skin tissue resulting in accelerated tissue healing.

RF skin treatment devices with relatively large electrodes used for skin firming or skin tightening, such as the STOP device of Pollagen and the Newa device of Endymed, require that a user applies a relatively large amount of an electrical coupling gel onto the skin or onto the electrodes of the device before applying the device to the skin and starting the treatment. Due to the large spread of the coupling gel and the large size of the electrodes, a good electrical coupling will be provided between the electrodes and the skin. However, in skin treatments with small-size active electrodes as described in the co-pending patent application EP 14171193.7 mentioned herebefore, wherein the active electrodes have a diameter of less than 2 mm, the depth of the thermal lesions generated by the RF energy is relatively small and the lesions are generated more superficially. As a result, if a relatively thick layer of a coupling gel were to be applied, a substantial part of the RF energy would be deposited in the coupling gel layer, which would reduce the depth in the skin at which the thermal lesions could be created. Additionally, the depth and size of the thermal lesions would strongly depend on the thickness and homogeneity of the gel layer, so that local variations of the thickness of the gel layer would result in an inhomogeneous depth and size of the pattern of lesions formed in the skin. Furthermore, as a result of the microstructures and topology of the skin surface, uniform electrical contact between the active electrode and the skin is difficult to obtain. The microscopic fluctuations of the roughness of the stratum corneum due to vertically stacked corneocytes are typically in the order of 1 µm to 10 µm. These fluctuations will result in an uneven distribution of the field lines from the active electrode into the skin and will potentially result in local hotspots below the electrodes and, thereby, in uncontrolled occurrence of skin tissue ablation.

US-A-2014/0207217 discloses a radio-frequency skin treatment device comprising a plurality of annular active and return electrodes. In certain embodiments, at least one of the electrodes is made of plastic, for example polycarbonate plastic, coated by a conductive coating.

WO-A-2012/023129 discloses an apparatus for personal aesthetic skin treatment including a carrier with a plurality of voltage applying electrodes located on a grid. In an embodiment, resilient electrodes are used to conform to the skin relief more easily and to enable better contact with the skin. The resilient electrodes are produced by coating copper electrodes by a conductive and resilient coating such as for example a conductive silicone.

WO-A-2010/093319 discloses a device intended to be attached directly or indirectly to skin, for example the cannulas of a dialysis machine. The device comprises a first layer which comprises an electrochemically active adhesive and a second layer which is in electrical contact with the first layer. The device can be attached to the skin by means of a DC current source by bringing a first terminal of the source into electrical contact with the skin and by bringing a second terminal of the source into electrical contact with the second layer of the device.

US-A-2004/0162602 discloses a surface electrode for long-term delivery of an electrical signal to a skin surface of a patient, including a metal foil layer for receiving an electrical signal from a power source or signal generator via conducting wires. Attached to the metal foil layer and disposed between the metal foil layer and the skin surface is a thin at least partially conductive surface layer. In an embodiment the surface layer is made of a hydrophilic gel. In another embodiment the surface layer consists of artificial skin. A partially conductive gel may be applied to the surface layer to improve the electrical contact with the skin surface.

WO-A-2012/073232 discloses a body shaping RF device comprising a segmented electrode having an array of energy applying surfaces mounted on a substrate via at least one electro-mechanical energy converting element. In an embodiment an adhesive coupling gel is applied manually or from a gel dispenser included in or attached to the electrode through pores in the substrate. Activation of the electro-mechanical energy converting elements brings about a redistribution of the skin surface under the electrode and also urges the applied gel along recesses in the electrode for further improving the electrode-skin contact and adhesion.

WO-A-2014/160848 discloses an electrode to apply non-invasive electrotherapy to a patient's body. In an embodiment the electrode comprises a base layer and a metal-coated area disposed on a bottom surface of the base layer. Beneath a bottom surface of the metal-coated area a gel layer is disposed which may extend beyond the perimeter of the metal-coated area to prevent unintentional direct contact of the metal-coated area with the patient's skin. The gel layer may be pre-fabricated as part of the electrode. An additional adhesive peripheral layer may be disposed directly beneath the bottom surface of the base layer around the gel layer to ensure secure attachment of the electrode to the skin.

WO-A-81/00785 discloses a cohesive non-sticky electrically conductive gel for facilitating low resistance contact between a metal electrode and a biological body. The gel comprises an aqueous solution of up to saturated concentrations of ionized salts as the conducting agent, a natural gum capable of cross-linking, and a cross-linking material which provides the electrically conductive gel with sufficient internal strength to remain cohesive without reinforcement. The gel has good electrical characteristics and improved physical properties which prevent the gel from leaving a messy residue on the skin of the patient or on the electrode.

SUMMARY OF THE INVENTION

It is an object of the present invention to provide a device for RF skin treatment, having a relatively small active electrode, with an improved coupling member for electrically coupling at least the active electrode to the skin, which enables the creation of more reproducible and uniform thermal lesions having well-defined depths and sizes.

According to a first aspect of the invention, the above-mentioned object is achieved by means of a device for radio-frequency (RF) skin treatment comprising an active electrode arranged on an operational side of the device and having a first skin contact surface for electrical contact with a skin of a user during use; a return electrode arranged on the operational side and having a second skin contact surface for electrical contact with the skin of the user during use, the second skin contact surface being at least five times larger than the first skin contact surface; an RF generator arranged to supply an RF treatment voltage between the active electrode and the return electrode when the active electrode and the return electrode are in electrical contact with the skin, so as to heat the skin below the active electrode; and a coupling member adapted to be arranged on the first skin contact surface and comprising an electrically conductive material for electrically coupling the active electrode to the skin, wherein the coupling member comprises a first layer of a first electrically conductive material adapted to be arranged on the first skin contact surface, and a second layer of a second electrically conductive material, different from the first material, arranged on the first layer, on a side of the first layer remote from the first skin contact surface, wherein the first layer has a thickness in a range from 10 μm to 100 μm and the first material has a modulus of elasticity of at least 100 kPa, and wherein the second layer has a thickness of 10 μm or less and the second material has a viscosity of 1,000 CPS or less. Because the first layer has a thickness in said range from 10 μm to 100 μm and the first material has said relatively high modulus of elasticity, the first layer ensures that, when the user holds the device against the skin surface with a pressure that can be expected under normal or prescribed operational conditions, variations of the distance between the skin contact surface of the active electrode and the skin surface, which occur as a result of deformations of the first layer as a result of said pressure or variations thereof, will remain within an acceptably small range, so that variations of the depth and sizes of the thermal lesions, which may occur as a result of the variations of said distance, will also remain within an acceptably small range. Because the second layer has a relatively small thickness, the second layer will only have a very limited or negligible influence on the distance between the skin contact surface of the active electrode and the skin surface. Because the second material has a relatively low viscosity, the second material, which will come into contact with the skin surface when the device is pressed against the skin, will easily spread into the microstructures present in the skin surface. As a result, during use the second layer fills the gaps between the micro-structured skin surface and the first layer and provides an improved and more homogeneous electrical contact between the skin contact surface of the active electrode and the skin surface, without substantially increasing or influencing the distance between the skin contact surface of the active electrode and the skin surface. In this way, an improved and reproducible electrical coupling is achieved between the active electrode and the skin surface, which enables the formation of reproducible skin lesions having well-defined depths and sizes.

It is noted that, as regards the coupling member and the first layer of the coupling member, the expression "adapted to be arranged on the first skin contact surface" covers embodiments wherein the coupling member is arranged on the first skin contact surface and embodiments wherein the coupling member is provided as a separate unit that can be arranged on the first skin contact surface by the user, for example as a disposable product.

In an embodiment of the device for RF skin treatment according to the invention, the first material is a solid material. The use of a solid material for the first material of the first layer has the advantage that, when the coupling member is pressed against the skin during use, the first layer of the coupling member will be locally slightly indented, but will not spread out in directions along the skin surface as would be the case when using for example a viscous liquid. As a result, the first material ensures a relatively limited variation of the thickness of the coupling member and of the distance between the skin contact surface of the active electrode and the skin surface. The first material for example comprises silicone rubber, polyurethane, silicone elastomer or other elastomeric materials. Alternatively, the first material may comprise a solid gel or a hydrogel having a modulus of elasticity within the range according to the present invention.

In a preferred embodiment of the device for RF skin treatment according to the invention, the first layer has a thickness in a range from 10 μm to 20 μm. A thickness of the first layer within this range provides an optimal electrical coupling of the active electrode to the skin and an optimal formation of uniform non-ablative thermal lesions, in particular for a relatively small-sized active electrode having a diameter of 1 mm or smaller used for skin rejuvenation.

In an embodiment of the device for RF skin treatment according to the invention, the second material comprises a viscous liquid. The use of a viscous liquid for the second material of the second layer has the advantage that, when the coupling member is pressed against the skin during use, the viscous liquid of the second layer of the coupling member will easily spread into the microstructures present in the skin surface and, thereby, homogeneously fill the gaps present between the micro-structured skin surface and the first layer of the coupling member. As a result, the second material ensures an optimal electrical coupling between the first layer of the coupling member and the skin surface. The viscous liquid is for example oil-based or water-based. The second material for example comprises a solid gel, a hydrogel, and/or an ionic gel (i.e. a solid gel with an electrolyte), having a viscosity within the range according to the present invention.

In a preferred embodiment of the device for RF skin treatment according to the invention, the first material and the second material each have an electrical conductivity in a range from 0.01 to 0.25 S/m for an RF frequency of 1 MHz. An electrical conductivity of the first and second materials in this range matches or nearly matches a range of the electrical conductivities of the stratum corneum and the epidermis of the skin. This further improves the electrical coupling between the active electrode and the skin, in particular in combination with a proper thickness of the coupling member, and thereby further improves the reproducibility of the thermal lesion formation.

In particular, the coupling member provides improved reproducibility of the thermal lesion formation in embodiments of the device for RF skin treatment according to the invention, wherein the first skin contact surface of the active electrode has a largest dimension of 2 mm or less. In such embodiments, the depth of the high-density portion of the RF field suitable for the formation of thermal lesions is relatively small, so that thermal lesions are formed superficially in the skin, in particular at locations immediately below the active electrode. The depth and sizes of such superficial lesions are relatively sensitive to variations of the distance between the skin contact surface of the active electrode and the skin surface. Given this sensitivity, the coupling member with the first and second layers according to the invention will greatly reduce any variations of the depth and sizes of the thermal lesions, as a result of its ability to limit variations of the distance between the active electrode and the skin surface during use.

In an embodiment of the device for RF skin treatment according to the invention, the coupling member is also adapted to be arranged on the second skin contact surface of the return electrode for electrically coupling the return electrode to the skin. This further improves electrical contact between the electrode system and the skin. In this embodiment, the coupling member preferably comprises separate coupling member portions, each having first and second layers in accordance with the invention, provided on the active electrode and on the return electrode. Alternatively, the coupling member comprises portions for electrical contact with the active electrode and the return electrode, wherein said portions are electrically isolated but provided on a common carrier.

In a specific embodiment of the device for RF skin treatment according to the invention, the device comprises a housing, a dispensing system arranged in the housing and configured to hold the second material, a rotatable body rotatably arranged inside the housing, wherein the active electrode and the return electrode are arranged on the rotatable body, and a rotation mechanism configured to rotate the rotatable body into a first position, wherein the active electrode and the return electrode are in communication with the dispensing system, and into a second position, wherein the active electrode and the return electrode are arranged on the operational side of the device. In this embodiment, the active electrode and the return electrode can automatically and repeatedly be provided with the second material, for example in between consecutive treatment steps at different positions on the skin. Thus, the first layer of the coupling member may stay on the electrodes during consecutive treatment steps, while the second material, which may remain on the skin after each treatment step, may be replenished.

According to a second aspect of the invention, the object of the invention is achieved by means of a coupling arrangement comprising a coupling member configured to be arranged on a skin contact surface of an electrode of a radio-frequency (RF) skin treatment device for electrically coupling the electrode to a skin of a user, wherein the coupling member comprises a first layer of a first electrically conductive material configured to be arranged on the skin contact surface via a first side of the first layer, and a second layer of a second electrically conductive material, different from the first material, arranged on the first layer, on a second side of the first layer opposite to the first side, wherein the first layer has a thickness in a range from 10 μm to 100 μm and the first material has a modulus of elasticity of at least 100 kPa, and wherein the second layer has a thickness of 10 μm or less and the second material has a viscosity of 1,000 CPS or less.

In an embodiment of the coupling arrangement according to the invention, the first material is a solid material. In a further embodiment of the coupling arrangement according to the invention, the second material is a viscous liquid. In a yet further embodiment of the coupling arrangement according to the invention, the first material and the second material each have an electrical conductivity in a range from 0.01 to 0.25 S/m for an RF frequency of 1 MHz.

In a preferred embodiment of the coupling arrangement according to the invention, a removable cover layer is arranged on the second layer, on a side of the second layer remote from the first layer. The removable cover layer protects the coupling member before it is used on the RF skin treatment device. In particular, the cover layer protects the second material from being unintentionally removed from the coupling member before it is actually used on the RF skin treatment device. The user may have to remove the cover layer from the coupling member before the actual use of the coupling member on the RF skin treatment device.

Further preferred embodiments of the device for RF skin treatment according to the invention and of the coupling arrangement according to the invention are described in the appended claims.

BRIEF DESCRIPTION OF THE DRAWINGS

These and other aspects of the invention will be apparent from and elucidated further with reference to the embodiments described by way of example in the following description and with reference to the accompanying drawings, in which FIG. 1 schematically shows a cross section of a device for RF skin treatment according to the invention.

The figures are purely diagrammatic and not drawn to scale. In the figures, elements which correspond to elements already described may have the same reference numerals.

DETAILED DESCRIPTION OF THE EMBODIMENTS

Figure 1:
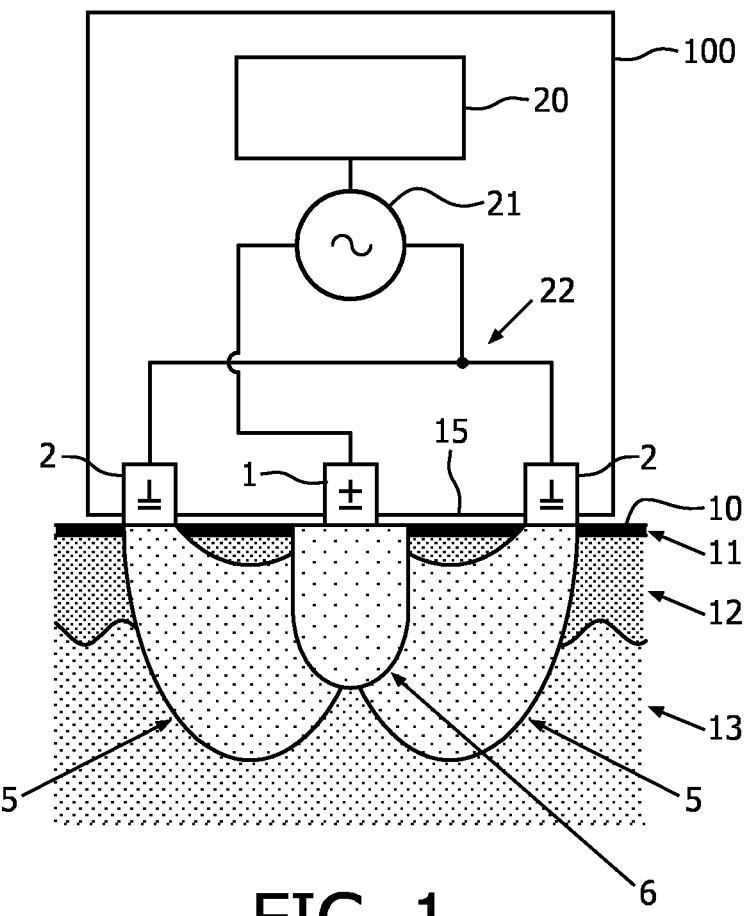

FIG. 1 schematically shows a cross section of a device 100 for radio-frequency (RF) skin treatment according to the state of the art. The device 100 comprises an inner active electrode 1 and an annular outer return electrode 2 (see also FIG. 2) surrounding the active electrode 1, wherein the active electrode 1 and the return electrode 2 are arranged on an operational side 15 of the device 100. The device 100 also comprises an electronic controller 20 and a radio-frequency (RF) generator 21 connected to the active electrode 1 and the return electrode 2 by electric wires 22. In FIG. 1, the electrodes 1, 2 are placed on a skin surface 10, the skin comprising the stratum corneum 11, the epidermis 12 and the dermis 13. When powered by the generator 21, the active electrode 1 and the return electrode 2 generate RF electric field lines 5 within the skin. Due to the applied RF voltage in combination with the skin impedance, heat is generated within the skin which, in this example, results in the generation of a non-ablative thermal lesion 6, in particular when the temperature of the skin reaches a level above 65° C. but below 100° C. The electronic controller 20 is arranged to control the RF generator 21.

Figure 2:
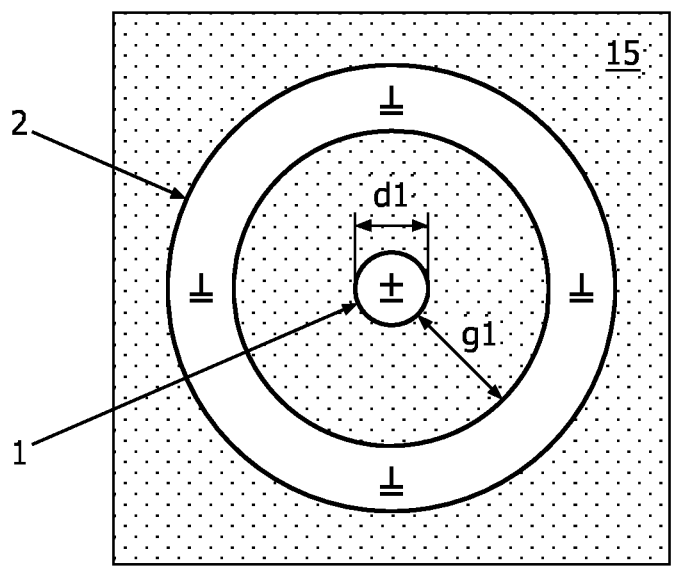
FIG. 2 shows a top view of an electrode configuration of the device of FIG. 1, with an inner active electrode surrounded by an annular outer return electrode.

FIG. 2 shows a top view of the electrode configuration of the device of FIG. 1, with the inner active electrode 1 being surrounded by the annular return electrode 2. The inner active electrode 1 is located in the center of the annular return electrode 2. The specific electrode configuration shown in FIG. 2 is referred to as a centro-symmetric electrode configuration. The first skin contact surface of the inner active electrode 1 may have a diameter $d_1$ for example in a range of 200 μm to 500 μm. A second skin contact surface of the return electrode 2 is typically at least five times larger than the first skin contact surface of the active electrode 1. A distance between the inner active electrode 1 and the annular return electrode 2 is referred to as the gap $g_1$. The gap $g_1$ is defined as the minimal distance between a point on the outer edge of the inner active electrode 1 and a point on the inner edge of the annular return electrode 2. For the centro-symmetric electrode configuration with a diameter $d_1$ as described herebefore, a typical value for the gap $g_1$ lies in a range of 0.1 mm to 10 mm.

To create multiple thermal lesions simultaneously, the device 100 may comprise a plurality of active electrodes 1 and a plurality of return electrodes 2, wherein each of the plurality of return electrodes surrounds a respective one of the plurality of active electrodes. The return electrodes may border each other, so as to form a lattice structure, or they may just be electrically coupled.

The device 100 can be used to create thermal lesions in the skin tissue for the purpose of skin rejuvenation. When a relatively low RF voltage is used (preferably less than 75 V), the device 100 is very suitable for home use without the need for professional assistance. A user may apply an electrically conductive coupling gel to the skin to improve electrical coupling between the active electrode and the skin. In view of the relatively small diameter of the active electrode (for a centro-symmetric electrode configuration this diameter is typically less than 2 mm), the concentrated portion of the RF electrical field which generates the thermal lesion in the skin is rather superficial as compared to electrode configurations having relatively large active electrodes. This will result in the formation of thermal lesions immediately below the active electrodes, while the skin tissue below the return electrodes will be unaffected. When using a plurality of active electrodes surrounded by return electrodes, a pattern of isolated superficial thermal lesions is generated, which are each surrounded by healthy skin tissue, which will accelerate the healing of the skin after the treatment. This is also known as fractional RF skin treatment.

In view of the superficial position of the thermal lesions, i.e. the small depth of the thermal lesions below the skin surface, a substantial part of the RF electrical energy will be deposited in the coupling gel layer, which further limits the depth at which the thermal lesions can be created. Additionally, variations in the thickness of the coupling gel layer will strongly influence the depth of the created thermal lesions. Furthermore, as a result of the microstructures present in the skin surface, i.e. the topology of the skin surface, a uniform electrical contact between the active electrode and the skin is difficult to obtain. To better understand these problems, the inventors performed computer simulations with respect to a centro-symmetric electrode configuration, as shown in FIG. 3.

Figure 3:
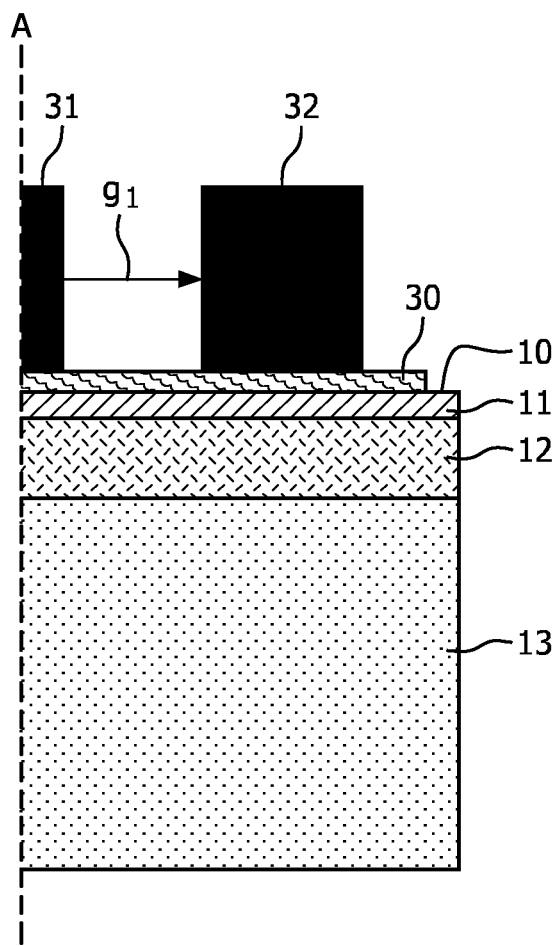
FIG. 3 schematically shows a centro-symmetric electrode configuration used for computer simulations of a device for RF skin treatment according to the invention.

In FIG. 3, line A indicates an axis of symmetry positioned in the centre of the active centre electrode 31. A diameter of the active electrode may be e.g. 400 μm. An annular return electrode 32 is arranged concentrically around the active electrode 31. A skin surface 10 is provided, wherein the skin has separate layers including the stratum corneum 11 with a thickness of e.g. 40 μm, the epidermis 12 with a thickness of e.g. 160 μm, and the dermis 13. A coupling member 30 is arranged between the electrodes 31, 32 and the skin surface 10. In this example, the gap $g_1$ between the active centre electrode 31 and the annular return electrode 32 is 1.3 mm. The RF treatment voltage was selected from a range of 40 Vrms to 50 Vrms and the treatment time was selected from a range of 75 ms to 150 ms. The thickness of the coupling member 30 was varied and, furthermore, the stratum corneum 11 was modelled both in a wet condition and a dry condition. In the following examples, discussed with reference to FIGS. 4A-4D, the coupling member 30 is modelled and provided in different ways.

Figure 4A:
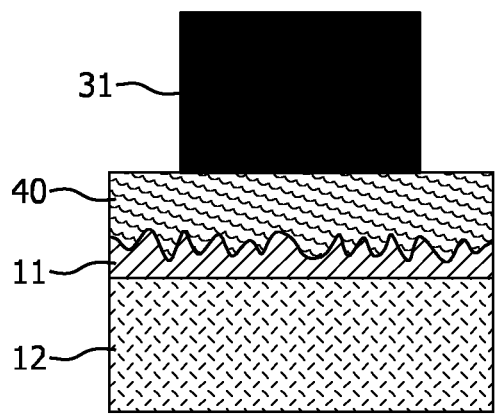
FIG. 4A schematically shows an example of an active electrode with a relatively thick layer of a coupling gel between the active electrode and the skin.

FIG. 4A schematically shows an example wherein a relatively thick layer of a coupling gel 40 is applied between the active centre electrode 31 and the skin. FIG. 4A also shows the stratum corneum 11 and the epidermis 12 of the skin. In this example, the coupling gel 40 comprises a liquid having a relatively low viscosity. By using a relatively thick layer of the coupling gel 40, all microstructures within the skin surface are easily filled, so that the coupling gel 40 provides good electrical contact between the active electrode 31 and the skin. However, when the active electrode 31 is applied onto the skin by applying a variable force, the thickness of the layer of the coupling gel 40 will change, which will influence the depth and sizes of the thermal lesions generated below the active electrode 31. In general, with a relatively thick layer of the coupling gel 40, the thickness of the layer and the depth and sizes of the thermal lesions cannot be sufficiently controlled.

Figure 4B:
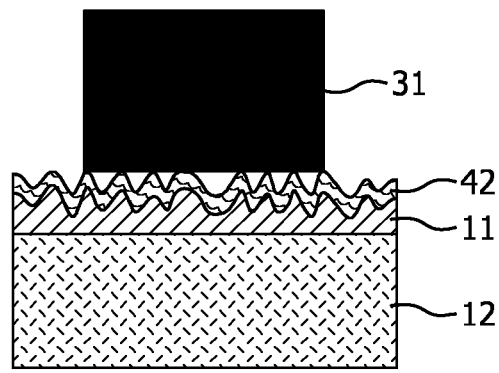
FIG. 4B schematically shows an example of an active electrode with a relatively thin layer of a coupling gel between the active electrode and the skin.

FIG. 4B schematically shows an example wherein a relatively thin layer of a coupling gel 42 is applied between the active electrode 31 and the skin. Also in this example, the coupling gel 42 comprises a liquid having a relatively low viscosity. In this example, the coupling gel 42 is spread homogeneously as a thin layer on the skin surface and within the microstructures present on the skin surface. Pressing the active electrode 31 on the skin will not provide the required good electrical contact between active electrode 31 and the skin surface, because air gaps remain present between the active electrode 31 and the skin, even when high pressures are applied on the active electrode 31.

Figure 4C:
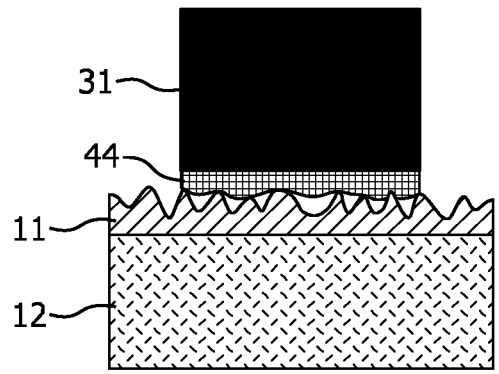
FIG. 4C schematically shows an example of an active electrode, wherein a thin layer of an elastically deformable solid material is applied between the active electrode and the skin.

FIG. 4C schematically shows an example wherein a thin layer of an elastically deformable and electrically conductive solid material 44 is applied between the active electrode 31 and the skin before the active electrode 31 is pressed against the skin. In the example of FIG. 4C, the solid material is e.g. applied in the form of a foil which is attached to the skin contact surface of the active electrode 31. When pressing the active electrode 31 onto the skin, the thickness of the layer of solid material 44 will vary only to a limited extent, so that the distance between the active electrode 31 and the skin is relatively well controlled. However, the electrical coupling between the active electrode 31 and the skin surface is not optimal in view of the many gaps that remain between the layer of solid material 44 and the skin surface as a result of the fact that the solid material 44 cannot locally adapt its shape to the microstructures present in the skin surface.

Figure 4D:
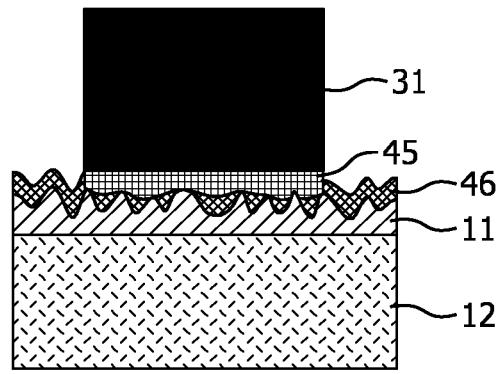
FIG. 4D shows an example of an active electrode in a device for RF skin treatment according to the invention, wherein a coupling member comprising a first layer of a first material having a relatively high modulus of elasticity and a second layer of a second material having a relatively low viscosity is applied between the active electrode and the skin.

FIG. 4D shows an example of the active electrode 31 in a device for RF skin treatment according to the present invention. In this example, a coupling member is applied between the skin contact surface of the active electrode 31 and the skin surface, wherein the coupling member comprises a first layer 45, which comprises a first electrically conductive material having a relatively high modulus of elasticity, and a second layer 46, which comprises a second electrically conductive material, different from the first material, having a relatively low viscosity. The first layer 45 is arranged on the skin contact surface of the active electrode 31, while the second layer 46 is arranged on the first layer 45, on a side of the first layer 45 remote from the skin contact surface of the active electrode 31. Simulations have shown that, when both the thicknesses of the first and second layers 45, 46, the modulus of elasticity of the first material, and the viscosity of the second material are within preferred ranges, a combination of such first and second layers 45, 46 of different materials results both in good electrical contact between the active electrode 31 and the skin and in a reproducible formation of the thermal lesions below the active electrode 31, as will be explained in more detail below when discussing the embodiments of the invention.

The examples shown in FIGS. 4A-4D can also be experimentally created by using a rigid transparent material representing the active electrode 31 (e.g. a glass plate) and by using different types of viscous coupling gels, coupling foils and/or hydrogels. By measuring the reflection of light from the surface of the glass plate when the glass plate is placed on the skin (e.g. on the top of a thumb, which is a micro-lined area of the skin surface having no hairs), the coupling between the glass plate and the skin can be inspected and the various examples can be visualized.

It is noted that, in practice, the thermal and electrical properties of the coupling member 30 between the active electrode 31 and the skin may vary within a very broad range depending on the composition of the materials used. In the performed simulations, a wide range of electrical conductivities was considered (from 0.01 to 1 S/m), while the thermal conductivity was maintained constant at about 0.5, which is a characteristic value for many aqueous gels. From the performed simulations, the inventors gained the following insights about the properties of the coupling member 30 between the active electrode 31 and the skin surface 10 required to create thermal lesions at the desired depth and with reproducible depth and sizes.

The first layer of the first electrically conductive material having the relatively high modulus of elasticity should have a thickness in a range from 10 μm to 100 μm. Preferably, the thickness of the first layer of the first material is in a range from 10 μm to 20 μm. If the first layer of the coupling member 30 is too thick, it will be heated too much and the depth of the thermal lesions becomes too small. To limit variations of the thickness of the first layer, which occur as a result of deformations of the first layer due to the pressure, or variations thereof, that can be expected under normal or prescribed operational circumstances, the modulus of elasticity of the first material should be at least 100 kPa. As a result, variations of the distance between the skin contact surface of the active electrode 31 and the skin surface will remain within an acceptably small range, so that variations of the depth and sizes of the thermal lesions, which may occur as a result of the variations of said distance, will also remain within an acceptably small range.

The second layer of the second electrically conductive material having the relatively low viscosity should have a thickness of 10 μm or less. With such a relatively small thickness, the second layer will only have a very limited or negligible influence on the distance between the skin contact surface of the active electrode 31 and the skin surface. Furthermore, the viscosity of the second material should be 1,000 CPS or less in order to cause it to spread sufficiently into the microstructures present in the skin surface and sufficiently fill the gaps between the micro-structured skin surface and the first layer under normal operating pressures exerted on the active electrode 31.

Preferably, the electrical conductivity of the first material and of the second material of the coupling member 30 are each within a range from 0.01 to 0.25 S/m, in particular for an RF frequency of 1 MHz, which also covers the electrical conductivities of the stratum corneum and of the epidermis. By matching the electrical conductivities of the first and second materials with the electrical conductivities of the stratum corneum and/or the epidermis, the electrical coupling between the active electrode 31 and the skin is further improved.

Preferably, the coupling member 30 is configured for moisturizing the skin in order to convert a relatively dry stratum corneum into a wetter stratum corneum. This will influence the lesion depth and size, i.e. a wetter stratum corneum will result in a deeper but also wider lesion as compared to a relatively dry stratum corneum.

When using a gel as the second material of the second layer, the vaporization of the gel during the treatment should not be too high in order to maintain the electrical coupling between the active electrode 31 and the skin, and also the thickness of the second layer, as constant as possible.

Figure 5:
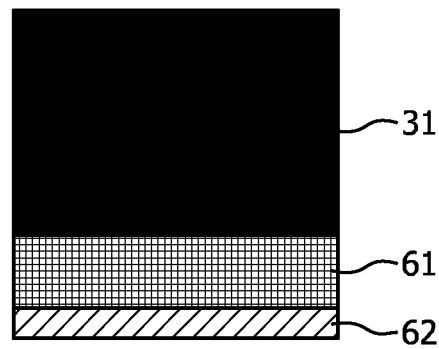
FIG. 5 schematically shows part of an embodiment of a device for RF skin treatment according to the invention, with a coupling member having a first layer arranged on the active electrode and a second layer arranged on the first layer.

FIG. 5 schematically shows part of an embodiment of a device for RF skin treatment according to the invention, comprising the characteristic properties as described herebefore. In this embodiment, the coupling member comprises a first layer 61, arranged on the active electrode 31, and a second layer 62 arranged on the first layer 61, on a side of the first layer 61 remote from the active electrode 31, wherein the first layer 61 comprises a first electrically conductive material and the second layer 62 comprises a second electrically conductive material different from the first material. The first layer 61 has a thickness in the range from 10 μm to 100 μm, preferably in the range from 10 μm to 20 μm. The modulus of elasticity of the first material of the first layer 61 is at least 100 kPa. The first layer 61 is for example a thin foil of a solid material. Suitable materials for the first layer 61 for example include silicone rubber, polyurethane, silicone elastomer or other elastomeric materials. Alternatively, the first material of the first layer 61 may comprise a hydrogel with a modulus of elasticity within the prescribed range. The second layer 62 has a thickness of 10 μm or less. The viscosity of the second material of the second layer 62 is 1,000 CPS or less. Preferably, the second material comprises a viscous liquid having a viscosity within the prescribed range. The viscous liquid may be an oil-based or water-based material, such as a low-viscosity gel. Alternatively, the second material may be a solid gel, a hydrogel, and/or an ionic gel having a viscosity within the prescribed range.

By pressing the active electrode 31 of FIG. 5 against the skin, the first layer 61 will be slightly indented, but will not spread out in directions along the skin surface. The second layer 62 may be applied either directly onto the skin or on the first layer 61 of the active electrode 31. By pressing the active electrode 31 against the skin, the low-viscosity second material of the second layer 62 will fill the gaps between the first layer 61 and the skin surface, thereby providing perfect electrical contact and coupling between the active electrode 31 and the skin (see also FIG. 4D). Furthermore, the low-viscosity second layer 62 will not substantially increase the distance between the active electrode 31 and the skin. The low-viscosity second material of the second layer 62 preferably has a high ability to spread out over the skin surface. Additionally, due to capillary forces of the low-viscosity second material of the second layer 62 between the first layer 61 and the skin, the microstructures of the skin surface will be flattened, leading to a less rough skin surface and an even more homogeneous distance between the active electrode 31 and the skin.

Thus, according to the invention, the first layer 61 having the first material with the relatively high modulus of elasticity mainly determines the thickness of the coupling member 30 in order to provide a relatively constant distance between the skin surface and the active electrode 31, while the second layer 62 having the second material with the low-viscosity second material provides filling of the microstructures of the skin surface in order to provide good electrical contact between the skin surface and the active electrode 31. The first and second layers 61, 62 preferably have electrical conductivities in a range comprising the electrical conductivities of the stratum corneum and the epidermis (0.01 S/m-0.25 S/m).

Figure 6:
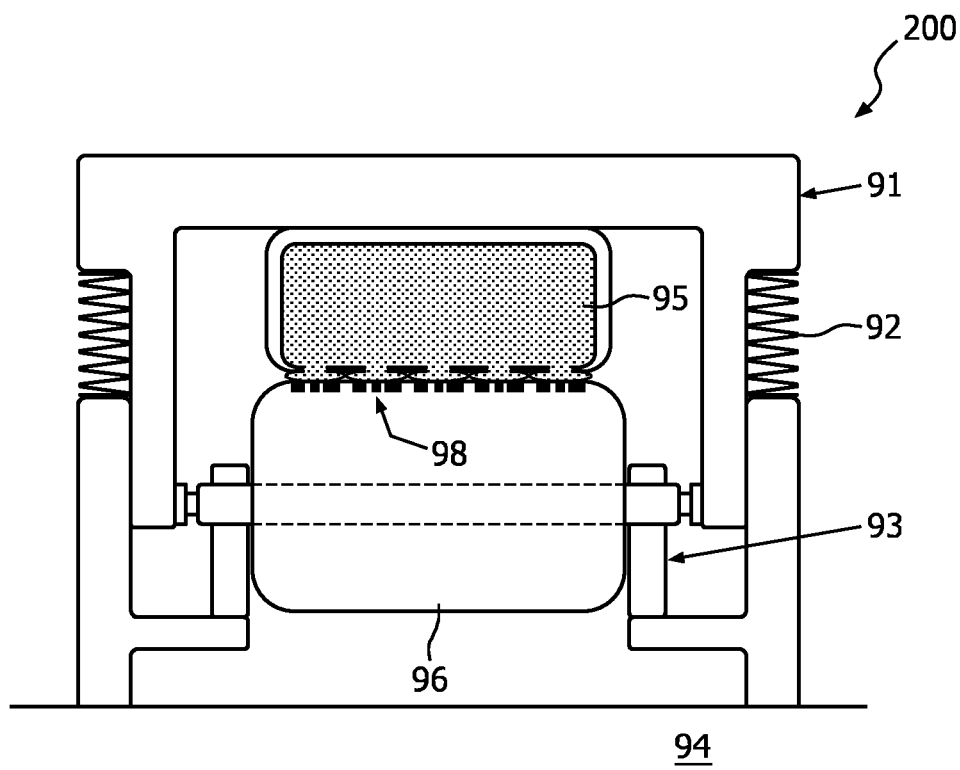
FIG. 6 schematically shows an embodiment of a device for RF skin treatment according to the invention comprising a housing, a rotation mechanism, a fluid dispensing system and RF electrodes arranged on a rotatable body.
Figure 7:
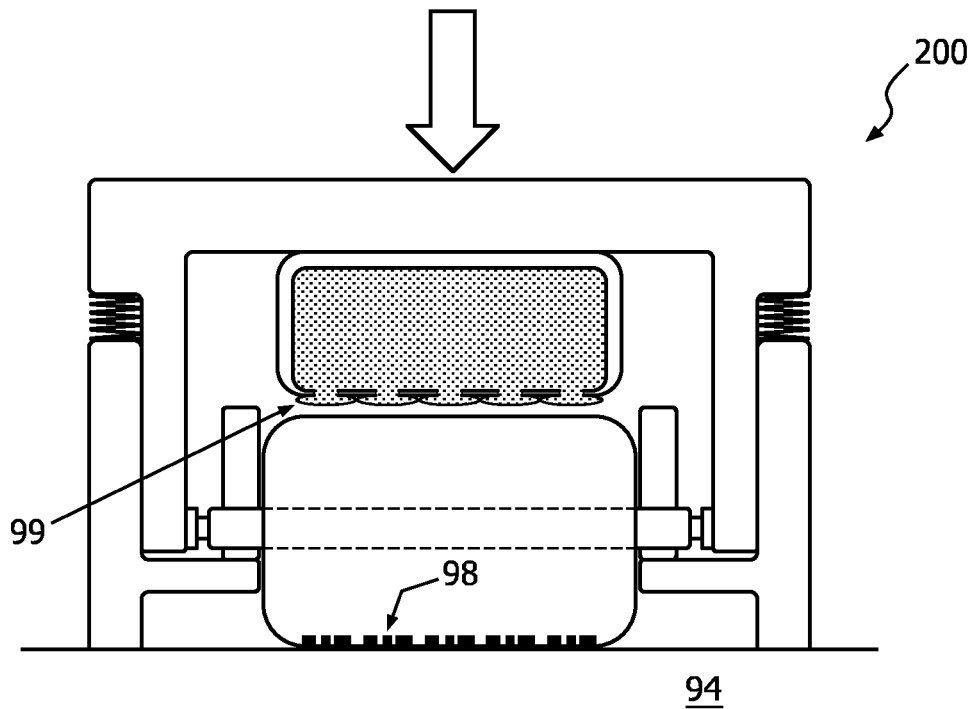
FIG. 7 shows the embodiment of FIG. 6, with the RF electrodes being pressed onto the skin.

As mentioned before, the second layer having the low-viscosity material can be applied on the first layer before use of the device, or the user can apply it directly on the skin before use of the device. According to a further embodiment of a device for RF skin treatment according to the invention, the first layer 61 is a layer of a solid material attached to the active electrode 31, while the second layer 62 is provided by bringing the active electrode 31 into contact with a dispensing system holding the low-viscosity second material, preferably in the form of a liquid. FIGS. 6 and 7 show an example of such a device.

FIG. 6 schematically shows an RF skin treatment device 200 comprising a housing 91, a spring system 92, a rotation mechanism 93, a fluid dispensing system 95 arranged in the housing 91, and a rotatable body 96, which is rotatably arranged inside the housing 91. A plurality of active electrodes and return electrodes, which are only schematically shown in FIG. 6, are arranged on an electrode side 98 of the rotatable body 96. The electrodes may have any kind of configuration comprising one or more active electrodes and one or more return electrodes. The return electrodes may be arranged next to the active electrodes or may surround the active electrodes. The device 200 can be placed on the surface of the skin 94, see FIG. 6. FIG. 7 shows the device 200 when pressed onto the skin 94. The arrow in FIG. 7 indicates a force that is exerted to press the device 200 onto the skin 94. Due to the force, an upper portion of the housing 91 is displaced relative to a lower portion of the housing 91 under deformation of the spring system 92. The displacement of the upper portion of the housing 91 activates the rotation mechanism 93, as a result of which the rotation mechanism 93 rotates the rotatable body 96 from a first position, shown in FIG. 6, into a second position, shown in FIG. 7. In the first position of the rotatable body 96, the electrode side 98 of the rotatable body 96 faces the fluid dispensing system 95 and the active and return electrodes on the electrode side 98 are in communication with the fluid dispensing system 95. The fluid dispensing system 95 comprises a reservoir for holding the second material comprising the low-viscosity fluid, which is supplied to the electrodes on the electrode side 98 in the first position of the rotatable body 96, for example via a fluid contact area 99 of the fluid dispensing system 95 which is indicated in FIG. 7. In the second position of the rotatable body 96, the electrode side 98 of the rotatable body 96 faces the skin 94, so that the active and return electrodes on the electrode side 98 are arranged on the operational side of the device 200 and can be brought into electrical contact with the skin 94. In the second position of the rotatable body 96 shown in FIG. 7, the fluid contact area 99 of the fluid dispensing system 95 is not in contact with the electrodes. In order to prevent dripping of the fluid from the fluid contact area 99 in the second position of the rotatable body 96, the fluid of the second material may be selected to have a suitable surface tension.

To exert optimal pressure on the coupling member 30 and thereby provide an optimal electrical coupling between the active electrode and the skin, an embodiment of an RF skin treatment device according to the invention is equipped with a pressure sensor to measure the pressure with which the user presses the device against the skin and to provide the user with feedback information or instructions about how to apply or maintain the right amount of pressure.

Figure 8:
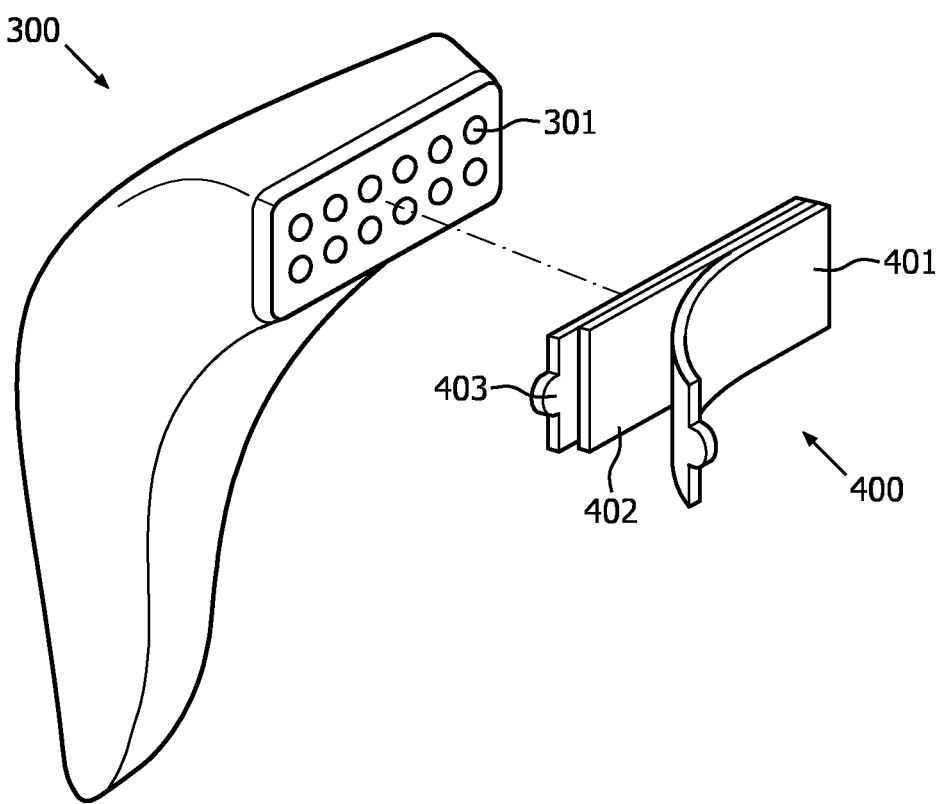
FIG. 8 shows a perspective view of an embodiment of a device for RF skin treatment comprising a disposable coupling arrangement according to the invention.

FIG. 8 shows a perspective view of an embodiment of a device 300 for RF skin treatment according to the invention, wherein the coupling member 402, 403 for electrically coupling the electrodes 301 to the skin is provided on a separate coupling arrangement 400 according to the invention. The device 300 comprises a plurality of electrodes 301. The coupling arrangement 400 is disposable and comprises a removable cover layer 401, a first layer 403 of a first electrically conductive material having a relatively high modulus of elasticity, and a second layer 402 having a second electrically conductive material, different from the first material, having a relatively low viscosity. The first layer 403 has a thickness in a range from 10 μm to 100 μm, and the second layer 402 has a thickness less than 10 μm. The modulus of elasticity of the first material is at least 100 kPa, while the viscosity of the second material is 1,000 CPS or less. The coupling arrangement 400 can be arranged on the skin contact surfaces of the electrodes 301 of the device 300, for example by sticking a first side of the first layer 403 of the coupling arrangement 400 on the operational side of the device 300 comprising the electrodes 301. The second layer 402 of the coupling arrangement is arranged on the first layer 403, on a second side of the first layer 403 opposite to the first said thereof. The removable cover layer 401 is arranged on the second layer 402 on a side of the second layer 402 remote from the first layer 403 and protects the second layer 402 when the coupling arrangement 400 is not in use. After arranging the coupling arrangement 400 on the skin surface, the user can peel off the cover layer 401 in order to expose the second layer 402 to the skin surface. By doing so, the electrodes 301 of the device 300 are provided with the conductive coupling member 402, 403 in accordance with the invention. The coupling arrangement 400 may comprise a removable cover layer 401 on each side, wherein one of the two cover layers has to be peeled off before arranging the coupling arrangement on the electrodes 301, and the other one of the cover layers has to be peeled off afterwards before bringing the device 300 into contact with the skin. It is noted that the cover layers may also be absent in a coupling arrangement according to the invention, and that the coupling member may be manufactured as a separate item, comprising the first and second layers, to be arranged on an RF skin treatment device and to be used in combination with an RF treatment device.

It should be noted that in the described embodiments, different electrode configurations can be used. As mentioned above, one or more inner active electrodes may be surrounded by annular or non-annular (e.g. square or rectangular) return electrodes. A return electrode may surround more than one active electrode. Alternatively, the active electrodes may be arranged in a one-dimensional array, wherein, adjacent to the array, a single elongated large return electrode is common to the active electrodes. Alternatively, two neighboring active electrodes may be separated by one of a plurality of return electrodes. Other electrode configurations with one or more active electrodes and one or more return electrodes are also possible. Furthermore, the coupling member may be used for electrically coupling the active electrode only to the skin, or for electrically coupling both the active electrode and the return electrode to the skin.

It is noted that, in this document, the word 'comprising' does not exclude the presence of elements or steps other than those listed, that the word 'a' or 'an' preceding an element does not exclude the presence of a plurality of such elements, and that any reference signs do not limit the scope of the claims. Further, the invention is not limited to the embodiments described herein, and the invention is present in each and every novel feature or combination of features described above or recited in mutually different dependent claims.

The invention claimed is:
1. A device for radio-frequency (RF) skin treatment, comprising:
an active electrode arranged on an operational side of the device and having a first skin contact surface for electrical contact with a skin of a user during use;
a return electrode arranged on the operational side and having a second skin contact surface for electrical contact with the skin of the user during use, the second skin contact surface being at least five times larger than the first skin contact surface;
an RF generator arranged to supply an RF treatment voltage between the active electrode and the return electrode when the active electrode and the return electrode are in electrical contact with the skin, so as to heat the skin below the active electrode;
a coupling arrangement comprising a coupling member adapted to be arranged on the first skin contact surface for electrically coupling the active electrode to the skin of the user, and
a dispensing mechanism, comprising:
a housing;
a fluid dispensing system arranged in the housing including a contact area, the fluid dispensing system comprising a reservoir for holding a material comprising a low-viscosity fluid;
a rotatable body rotatably arranged to rotate about a horizontal axis positioned in the housing, the rotatable body comprising an electrode side and a non-electrode side, with the active and the return electrodes arranged on the electrode side; and wherein an upper portion of the housing is displaceable relative to a fixedly positioned lower portion of the housing under deformation of a spring system, wherein displacement of the upper portion of the housing activates a rotation mechanism via a spring system to rotate the rotatable body from a first position into a second position, wherein said fluid dispensing system and said upper portion of the housing are displaced vertically under deformation of said spring system, wherein in the first position, the electrode side of the rotatable body faces the fluid dispensing system contact area to allow the active and the return electrodes to communicate with the fluid dispensing system contact area to supply the active and return electrodes on the electrode side with a low-viscosity fluid, and wherein in the second position, the electrode side of the rotatable body faces away from the fluid contact area of the fluid dispensing system and faces towards the skin of the user such that the active and return electrodes on the electrode side are arranged on the operational side of the device to allow electrical contact with the skin of the user.

2. The device according to claim 1, wherein the first skin contact surface has a largest dimension of 2 mm or less.

3. The device according to claim 1, wherein the coupling arrangement is adapted to be arranged on the second skin contact surface for electrically coupling the return electrode to the skin.

4. The device according to claim 1, wherein the coupling member comprises a first layer of a first electrically conductive material comprising a solid material.

5. The device according to claim 4, wherein the first electrically conductive material of the first layer comprises silicone rubber, polyurethane, silicone elastomer or other elastomeric materials.

6. The device according to claim 4, wherein the first layer has a thickness in a range from 10 μm to 20 μm.

7. The device according to claim 4, wherein the coupling member comprises a second layer of a second electrically conductive material comprising a viscous liquid.

8. The device according to claim 7, wherein the second electrically conductive material of the second layer comprises a solid gel, a hydrogel, and/or an ionic gel.

9. The device according to claim 8, wherein the first electrically conductive material and the second electrically conductive material each have an electrical conductivity in a range from 0.01 to 0.25 S/m for an RF frequency of 1 MHz.

10. The device according to claim 8, wherein a removable cover layer is arranged on the second layer, on a side of the second layer remote from the first layer.

11. A device for radio-frequency (RF) skin treatment, comprising:
a plurality of active electrodes arranged on an operational side of the device and having a first skin contact surface for electrical contact with a skin of a user during use;
a plurality of return electrodes arranged on the operational side and having a second skin contact surface for electrical contact with the skin of the user during use, the second skin contact surface being at least five times larger than the first skin contact surface;
an RF generator arranged to supply an RF treatment voltage between the plurality of active electrodes and the plurality of return electrodes when the plurality of active electrodes and the plurality of return electrodes are in electrical contact with the skin, so as to heat the skin below the active electrode;

a coupling arrangement comprising a coupling member adapted to be arranged on the first skin contact surface for electrically coupling the active electrode to the skin of the user, and
a dispensing mechanism, comprising:
a housing;
a fluid dispensing system arranged in the housing including a contact area, the fluid dispensing system comprising a reservoir for holding a material comprising a low-viscosity fluid;
a rotatable body rotatably arranged to rotate about a horizontal axis in the housing, the rotatable body comprising an electrode side and a non-electrode side, with the plurality of active and the return electrodes being arranged on the electrode side; and
wherein an upper portion of the housing is displaceable relative to a stationary lower portion of the housing under deformation of a spring system,
wherein each of said fluid dispensing system and upper portion of the housing are displaced vertically under deformation of said spring system,
wherein said vertical displacement of said combined unit activates a rotation mechanism configured to rotate the rotatable body from a first position into a second position,
wherein in the first position of the rotatable body, the electrode side of the rotatable body faces the fluid dispensing system contact area to allow the active and the return electrodes to communicate with the fluid dispensing system contact area to supply the electrodes on the electrode side with a low-viscosity fluid,
wherein in the second position of the rotatable body, the electrode side of the rotatable body faces away from the fluid contact area of the fluid dispensing system and towards the skin of the user such that the active and return electrodes on the electrode side are arranged on the operational side of the device to allow electrical contact with the skin of the user.

12. The device according to claim 11, wherein the first skin contact surface has a largest dimension of 2 mm or less.

13. The device according to claim 11, wherein the coupling member comprises a first layer of a first electrically conductive material comprising a solid material.

14. The device according to claim 13, wherein the first electrically conductive material of the first layer comprises silicone rubber, polyurethane, silicone elastomer or other elastomeric materials.

15. The device according to claim 13, wherein the first layer has a thickness in a range from 10 μm to 20 μm.

16. The device according to claim 13, wherein the coupling member comprises a second layer of a second electrically conductive material comprising a viscous liquid.

17. The device according to claim 16, wherein the second electrically conductive material of the second layer comprises a solid gel, a hydrogel, and/or an ionic gel.

18. The device according to claim 16, wherein a removable cover layer is arranged on the second layer, on a side of the second layer remote from the first layer.

19. A dispensing mechanism for use in a device for radio-frequency (RF) skin treatment, comprising: a housing including a displaceable upper portion and a fixedly positioned stationary lower portion;
a fluid dispensing system arranged in the housing including a contact area, the fluid dispensing system comprising a reservoir for holding a material comprising a low-viscosity fluid;

a rotatable body rotatably arranged to rotate around a horizontal axis, the rotatable body comprising an electrode side and a non-electrode side, with active and return electrodes arranged on the electrode side; and wherein an upper portion of the housing is displaceable relative to the lower portion of the housing under deformation of a spring system, wherein displacement of the upper portion of the housing activates a rotation mechanism via a spring system to rotate the rotatable body from a first position into a second position, wherein in a first position, the electrode side of the rotatable body faces the fluid dispensing system contact area to allow the active and the return electrodes to communicate with the fluid dispensing system contact area to supply the active and return electrodes on the electrode side with a low-viscosity fluid, and wherein in a second position, the electrode side of the rotatable body faces away from the fluid contact area of the fluid dispensing system and faces towards the skin of the user such that the active and return electrodes on the electrode side are arranged on the operational side of the device to allow electrical contact with the skin of the user.

* * * * *